(12) United States Patent
Song

(10) Patent No.: US 9,186,160 B1
(45) Date of Patent: Nov. 17, 2015

(54) PATIENT SPECIFIC INSTRUMENT FOR DURABLE RESURFACING HIP REPLACEMENT DEVICE

(71) Applicant: Benjamin Soo-Il Song, Los Angeles, CA (US)

(72) Inventor: Benjamin Soo-Il Song, Los Angeles, CA (US)

( * ) Notice: Subject to any disclaimer, the term of this patent is extended or adjusted under 35 U.S.C. 154(b) by 0 days.

(21) Appl. No.: 14/613,286

(22) Filed: Feb. 3, 2015

(51) Int. Cl.
*A61B 17/17* (2006.01)
*A61B 17/74* (2006.01)
*A61B 17/56* (2006.01)

(52) U.S. Cl.
CPC .............. *A61B 17/1717* (2013.01); *A61B 17/74* (2013.01); *A61B 17/742* (2013.01); *A61B 2017/568* (2013.01)

(58) Field of Classification Search
CPC .. A61B 17/1742; A61B 17/74; A61B 17/742; A61B 17/1717
See application file for complete search history.

(56) References Cited

U.S. PATENT DOCUMENTS

| | | | |
|---|---|---|---|
| 7,179,259 B1 * | 2/2007 | Gibbs | 606/64 |
| 2005/0171545 A1 * | 8/2005 | Walsh et al. | 606/72 |
| 2015/0182266 A1 * | 7/2015 | Jakob et al. | 606/280 |

* cited by examiner

*Primary Examiner* — Andrew Yang
(74) *Attorney, Agent, or Firm* — John K. Park; Park Law Firm

(57) ABSTRACT

A patient-specific instrument for durable resurfacing hip replacement device comprises a head-neck-area receiving inner portion, a top edge portion, an outer portion, one or more distal-head-neck-hole guiding pins, a femoral-shaft-hole guiding pin, and a vertical groove. The head-neck-area receiving inner portion is contoured to fit over a portion of head, neck, and upper shaft body of the femur. The one or more distal-head-neck-hole guiding pins are installed on the top edge portion, so as to work as a first reference line showing a first direction of a long nail portion of the durable resurfacing hip replacement device. The femoral-shaft-hole guiding pin is installed on the outer portion, so as to work as a second reference line showing a second direction of a lag screw portion of the durable resurfacing hip replacement device. The vertical groove is provided on the outer portion and aligned in parallel to the femoral-shaft-hole guiding pin.

10 Claims, 5 Drawing Sheets

PATIENT SPECIFIC INSTRUMENT FOR DURABLE RESURFACING HIP REPLACEMENT DEVICE

BACKGROUND OF THE INVENTION

The present invention relates to a patient specific instrument for a durable resurfacing hip replacement device. More particularly, this invention relates to a patient specific instrument for durable resurfacing hip replacement device, which helps a surgeon to prepare and operate the medical treatments related to the durable resurfacing hip replacement device.

Joint replacement may provide a dramatic improvement in the quality of life of patients with end stage of arthritis of the hip, but the medical processes are complicated and challenging to the patient and the surgeon in some senses.

Accordingly, a need for a patient specific instrument for a minimal invasive hip arthroplasty device has been present for a long time considering the expansive demands in the everyday life. This invention is directed to solve these problems and satisfy the long-felt need.

SUMMARY OF THE INVENTION

The present invention contrives to solve the disadvantages of the prior art.

An object of the invention is to provide a patient specific instrument for the durable resurfacing hip replacement device.

Another object of the invention is to provide a patient specific instrument for the durable resurfacing hip replacement device, which helps the surgeon in preparing and performing the durable resurfacing hip replacement.

An aspect of the invention provides a patient specific instrument for the durable resurfacing hip replacement device.

A patient-specific instrument for durable resurfacing hip replacement device comprises a head-neck-area receiving inner portion, a top edge portion, an outer portion, one or more distal-head-neck-hole guiding pins, one or more femoral-shaft-hole guiding pins, and a vertical groove.

The head-neck-area receiving inner portion is contoured to fit over a portion of head, neck, and upper shaft body of the femur, so as to maintain a stable spatial relationship with the femur.

The top edge portion extends from the head-neck-area receiving portion substantially perpendicularly to a plane defined by the head, neck, and shaft body of the femur.

The outer portion extends from the top edge portion substantially perpendicularly to the top edge portion.

The femoral-shaft-hole guiding pins are installed on the top edge portion, so as to work as a first reference line showing a first direction of a long nail portion of the durable resurfacing hip replacement device (hip arthroplasty device).

The one or more distal-head-neck-hole guiding pins are installed on the outer portion, so as to work as a second reference line showing a second direction of a lag screw portion of the durable resurfacing hip replacement device (hip arthroplasty device).

The vertical groove is provided on the outer portion and aligned in parallel to the femoral-shaft-hole guiding pin.

The one or more distal-head-neck-hole guiding pins, the one or more femoral-shaft-hole guiding pins, and the vertical groove are configured for helping a surgeon to install the durable resurfacing hip replacement device.

The patient-specific instrument may be customized to an individual patient.

The head-neck-area receiving inner portion, the top edge portion, the one or more distal-head-neck-hole guiding pins, the femoral-shaft-hole guiding pin, and the vertical groove of the patient-specific instrument may be customized by a computer navigated method.

The head-neck-area receiving inner portion of the patient-specific instrument may be customized to the individual patient.

A contour of the head-neck-area receiving inner portion of the patient-specific instrument may be determined and manufactured through an MRI/CT scan.

The patient-specific instrument may be made of plastic material.

The patient-specific instrument may comprises a head-and-neck-contouring part, an upper-femural-shaft-contouring part extending from the head-and-neck-contouring part, and an upper-femural-shaft-holding part extending from the upper-femural-shaft-contouring part.

The outer portions corresponding to the head-and-neck-contouring part and the upper-femural-shaft-contouring part meet each other by a first angle and the outer portions corresponding to the upper-femural-shaft-contouring part and the upper-femural-shaft-holding part meet each other by a second angle, such that the patient-specific instrument holds the portion of head, neck, and upper shaft body of the femur substantially stably.

The patient-specific instrument may further comprise a head-holding part extending from the head-and-neck-contouring part and following substantially up to a summit portion of the head.

The upper-femural-shaft-holding part may be configured to go around a corner of the upper shaft to the portion of the upper shaft covered by the head-neck-area receiving inner portion corresponding to the upper-femural-shaft-contouring part.

The patient-specific instrument may be applicable to a plurality of surgical approaches incluisic anterior-posterior or lateral surgical hip approaches.

The advantages of the present invention are: the patient specific instrument for a durable resurfacing hip replacement device according to the invention can provide:

(1) helping the surgeon in preparation of the resurfacing hip replacement;
(2) non-incisive preparation;
(3) helping the surgeon in performing of the resurfacing hip replacement;
(4) one or more distal-head-neck-hole guiding pins;
(5) femoral-shaft-hole guiding pin; and
(6) vertical groove aligned in parallel to the femoral-shaft-hole guiding pin.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION EMBODIMENTS OF THE INVENTION

The U.S. patent application Ser. No. 12/765,759 filed by the inventor on Apr. 22, 2010, titled "MINIMAL INVASIVE HIP ARTHROPLASTY DEVICE" and the U.S. Pat. No. 8,840,675 issued on Sep. 23, 2014, are hereby incorporated by reference.

Figure 1:
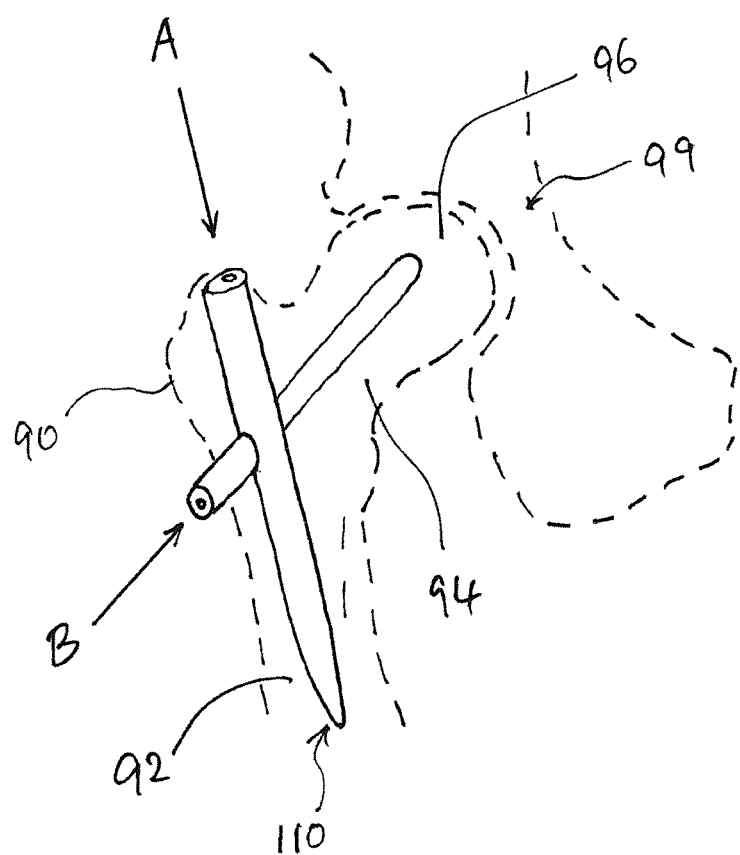
FIG. 1 is a perspective view showing directions mattered according to an embodiment of the present invention.

The minimal invasive hip arthroplasty device 110 is shown in FIG. 1. As shown, holes for the minimal invasive hip arthroplasty device 110 are needed through the neck 94, and the head 96 of the femur 90. The pelvis 99 is shown in connection with the head 96 for reference.

Therefore, in order to perform the operation, the surgeon needs to drill two holes for install the minimal invasive hip arthroplasty device 110.

However, since the exact shapes or dimensions of the femur 90 and the pelvis 99 are all different depending on patients, it is challenging and time-consuming for the surgeon to find out the specific dimensions and shapes and drill the needed holes correctly and fast.

The invention is to solve the above problems of prior arts.

Computer navigated patient specific custom mold is provided for durable resurfacing hip replacement device.

The device is prepared through MRI/CT scan and this device is patient specific accurate pin centering guide.

The device includes custom molded head & neck portion and distal head and neck pin guide holes and femoral shaft pin guide holes, vertical groove for edge hole check femoral shaft pin guide.

After surgical open the hip joint, the head and neck portion is placed in pre-navigated corresponding head and neck area, distally the vertical holes and groove guides femoral shaft pin placement and oblique hole guides femoral head and neck pin placement along the pins, make drill holes for resurfacing hip replacement procedure.

This device is applicable to all kinds of surgical approaches such as anterior-posterior or lateral surgical hip approaches. That is, since the surgeon knows the exact shapes and dimensions of the portion to operate well before opening the portion, it doesn't matter whether the operation would be performed in any directions.

An object of the invention is to provide a patient specific instrument 100 for the durable resurfacing hip replacement device 110.

Another object of the invention is to provide a patient specific instrument 100 for the durable resurfacing hip replacement device 110, which helps the surgeon in preparing and performing the durable resurfacing hip replacement.

An aspect of the invention provides a patient specific instrument 100 for the durable resurfacing hip replacement device 110 enabling the surgeon to perform the operation in any directions.

FIG. 1 shows directions mattered in the operation for the durable resurfacing hip replacement device 110. FIGS. 2 to 5 show a patient specific instrument 100 for a durable resurfacing hip replacement device 110 according to an embodiment of the present invention.

Figure 2:
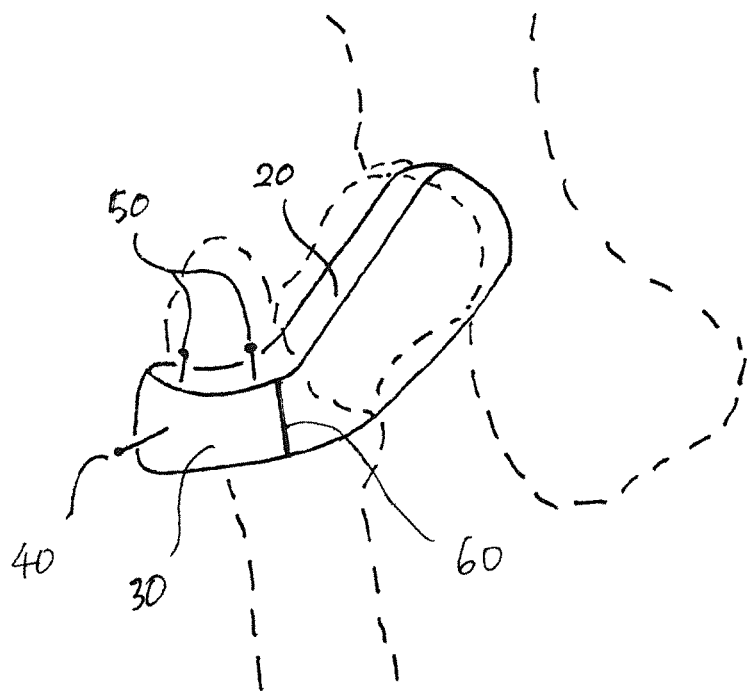
FIG. 2 is a perspective view showing a patient specific instrument for a durable resurfacing hip replacement device fitted to bones according to an embodiment of the present invention.
Figure 3:
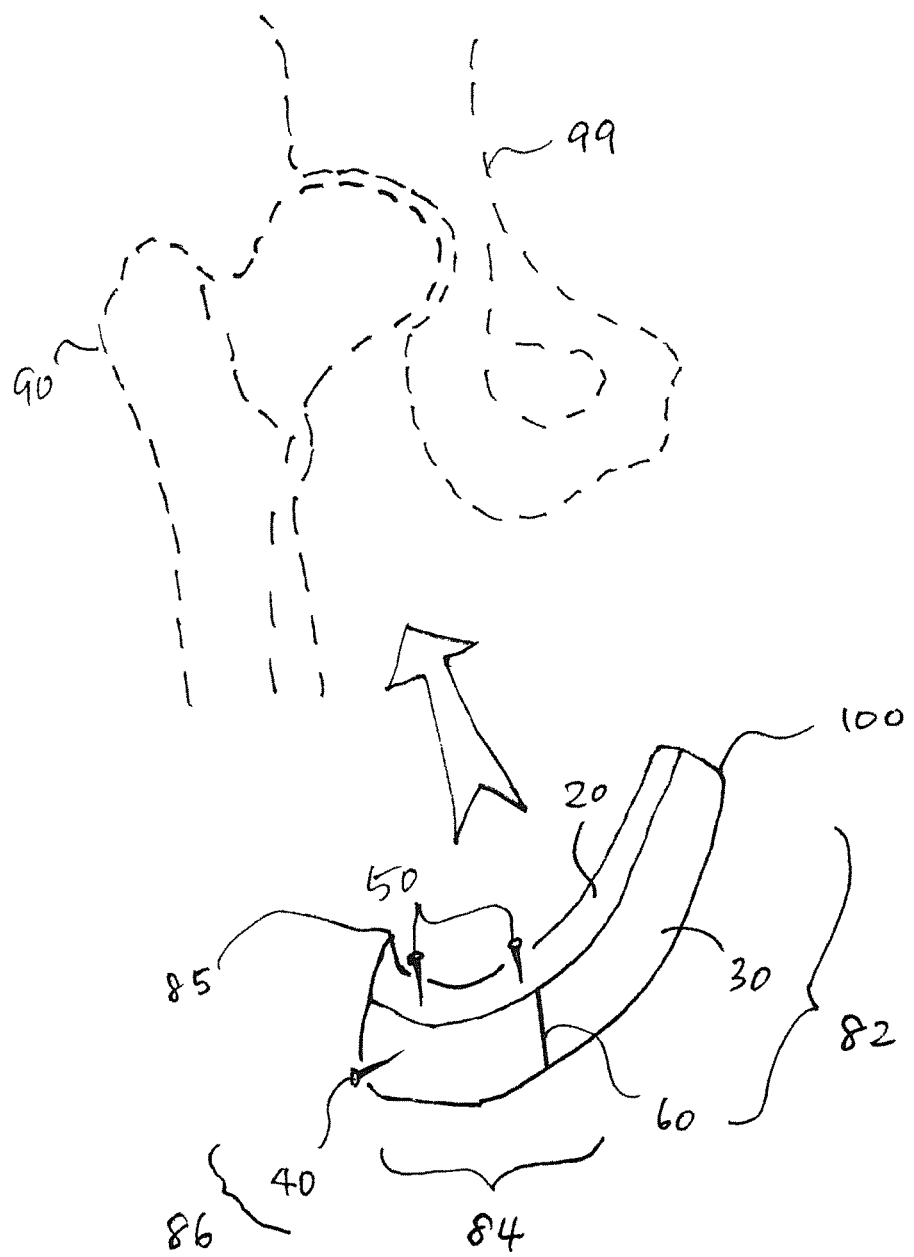
FIG. 3 is another perspective view showing a patient specific instrument for a durable resurfacing hip replacement device to be attached to the bones according to an embodiment of the present invention.
Figure 4:
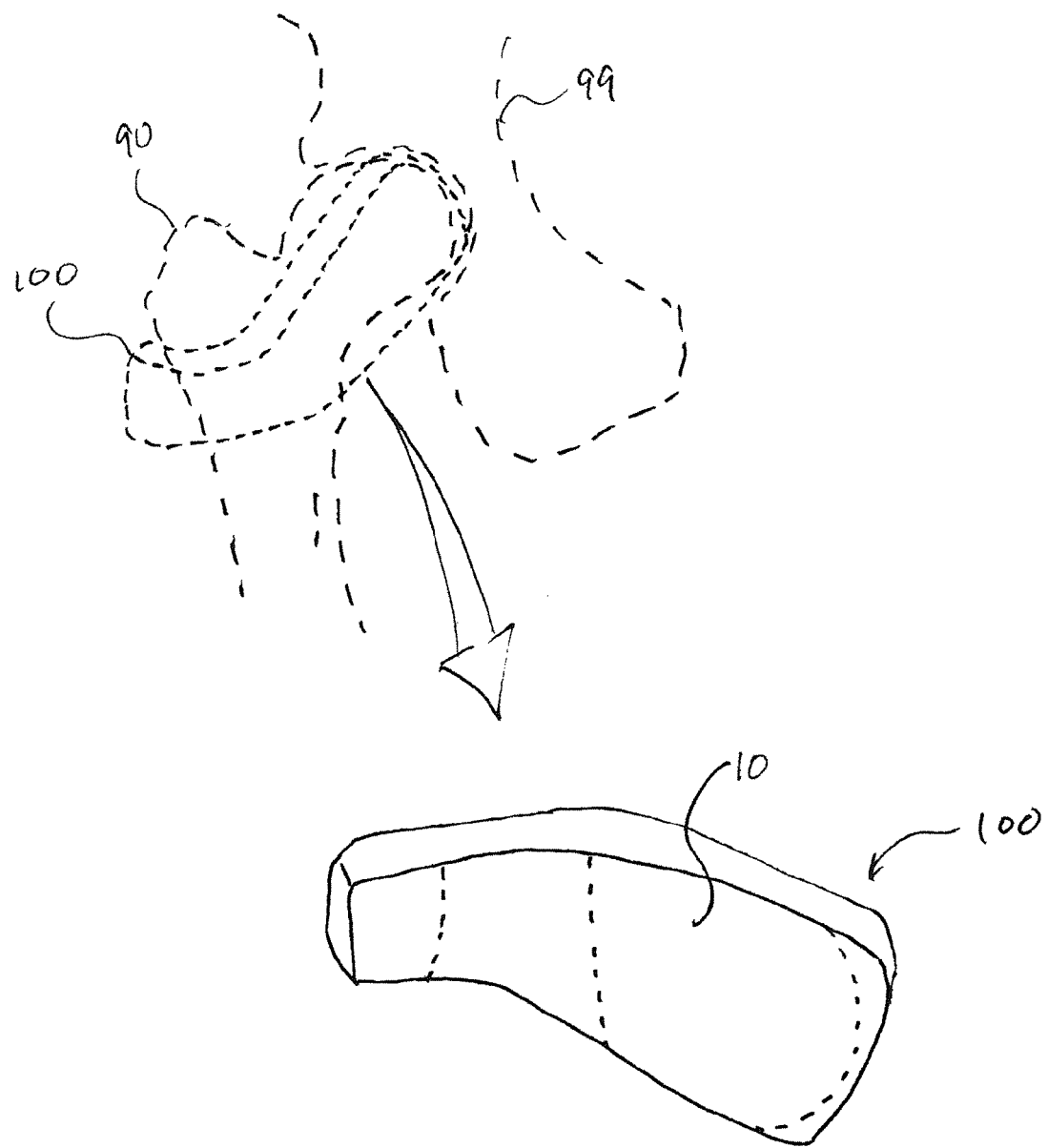
FIG. 4 is another perspective view showing the patient specific instrument for a durable resurfacing hip replacement device of FIG. 2 detached from the bones.
Figure 5:
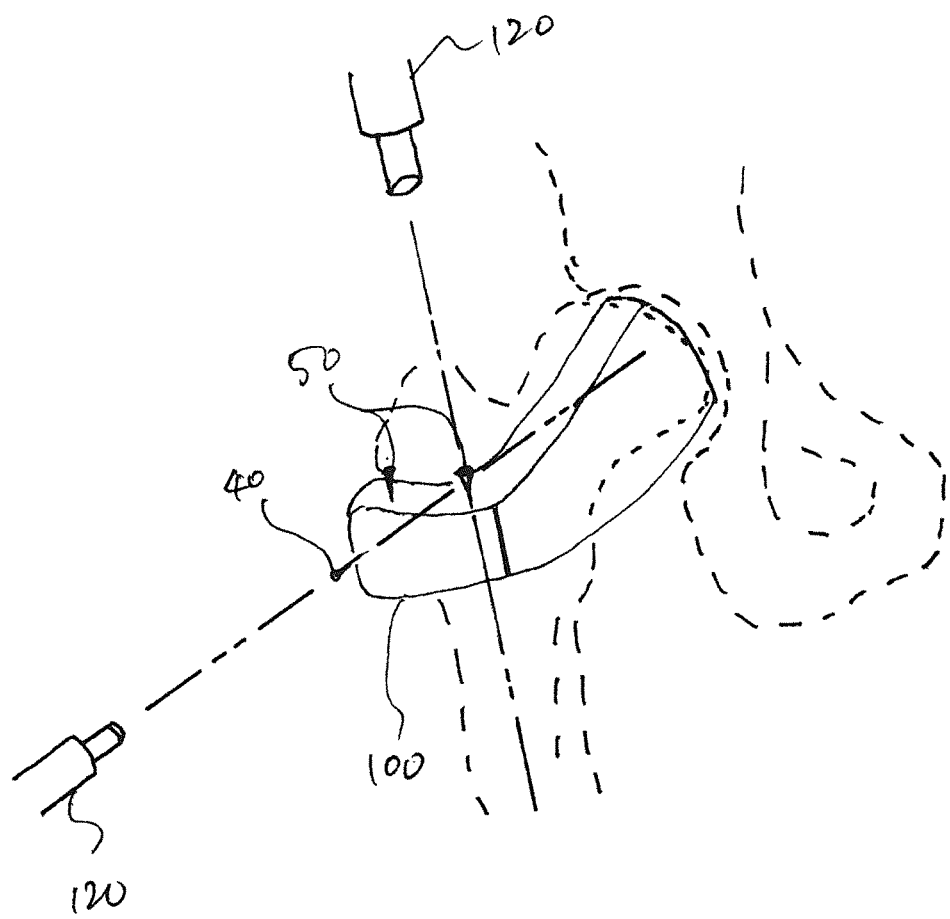
FIG. 5 is still another perspective view showing a patient specific instrument for a durable resurfacing hip replacement device fitted to the bones with directions aligned with pins in guiding drills according to an embodiment of the present invention.

A patient-specific instrument 100 for durable resurfacing hip replacement device 110 comprises a head-neck-area receiving inner portion 10, a top edge portion 20, an outer portion 30, one or more distal-head-neck-hole guiding pins 40, one or more femoral-shaft-hole guiding pins 50, and a vertical groove 60 as shown in FIGS. 2-4.

The head-neck-area receiving inner portion 10 is contoured to fit over a portion of head 96, neck 94, and upper shaft body of the femur 90 as shown in FIG. 4, so as to maintain a stable spatial relationship with the femur 90, when the surgeon opens the operation portion of the patient and engages the PSI 100 across the portion of head 96, neck 94, and upper shaft body of the femur 90.

The top edge portion 20 extends from the head-neck-area receiving portion 10 substantially perpendicularly to a plane defined by the head 96, neck 94, and shaft body 92 of the femur 90.

The outer portion 30 extends from the top edge portion 20 substantially perpendicularly to the top edge portion 20.

The femoral-shaft-hole guiding pins 50 are installed on the top edge portion 20, so as to work as a first reference line A showing a first direction of a long nail portion of the durable resurfacing hip replacement device 110 (hip arthroplasty device).

The one or more distal-head-neck-hole guiding pins 40 are installed on the outer portion 30, so as to work as a second reference line B showing a second direction of a lag screw portion of the durable resurfacing hip replacement device 110 (hip arthroplasty device).

In certain embodiments of the invention, the one or more distal-head-neck-hole guiding pins 40 are aligned with the central line of the head 96 and neck 94 of the femur 90. In the illustrated embodiments, there is provided only one distal-head-neck-hole guiding pin 40. If additional pins are needed or helpful, more of them can be disposed in any portions of the PSI 100.

The vertical groove 60 is provided on the outer portion 30 and aligned in parallel to at least one of the one or more femoral-shaft-hole guiding pins 40. The vertical groove 60 may guide the surgeon's drill 120 from another perspective direction that is convenient to the surgeon. Therefore, the direction of the vertical groove 60 may be substantially parallel to the direction A, or alternatively may be adjusted to the surgeon's personal perspective view in the operation.

The one or more distal-head-neck-hole guiding pins 40, the one or more femoral-shaft-hole guiding pins 50, and the vertical groove 60 are configured for helping a surgeon to install the durable resurfacing hip replacement device 110. Therefore, in the manufacturing process of the PSI 100, such personal dimension or geometry factors for a specific surgeon may be considered in the computer navigated designing of the PSI 100, using along with the 3D information of the patient obtained from the MRI/CT scans.

That way, the patient-specific instrument 100 may be customized to an individual patient.

The head-neck-area receiving inner portion 10, the top edge portion 20, the one or more distal-head-neck-hole guiding pins 40, the femoral-shaft-hole guiding pins 50, and the vertical groove 60 of the patient-specific instrument 100 may be customized by a computer navigated method. In certain embodiment, more than one vertical groove 60 may be provided.

The head-neck-area receiving inner portion 10 of the patient-specific instrument 100 may be customized to the individual patient, such that the PSI 100 fits to the operation portion of the patient and provides a firm base for determining and drilling the necessary holes for the operation.

A contour of the head-neck-area receiving inner portion 10 of the patient-specific instrument 100 may be determined and manufactured through an MRI/CT scans.

Through the MRI/CT scan, the exact bone structures of a specific patient can be obtained before the operation. The three-dimensional information from the MRI/CT scans can determine the positions and directions of the the one or more distal-head-neck-hole guiding pins, the femoral-shaft-hole guiding pin, and the vertical groove as well as the exact contours of the head-neck-area receiving inner portion. Therefore, the surgeon is able to know the exact positions and directions to drill through the bones.

All the three-dimensional information from the MRI/CT scan are stored and processed by an information processing devices such as a computer.

The patient-specific instrument 100 may be made of plastic material, but not limiting.

The patient-specific instrument 100 may comprises a head-and-neck-contouring part 82, an upper-femoral-shaft-contouring part 84 extending from the head-and-neck-contouring part 82, and an upper-femoral-shaft-holding part 86 extending from the upper-femoral-shaft-contouring part 84 as shown in FIG. 3. Especially, the patient-specific instrument 100 may comprise a holding portion 85, which extends from the upper-femoral-shaft-holding part 86 and goes around a corner of the shaft body 92 of the femur 90 so as to anchor the PSI 100, as shown in FIG. 3.

The outer portions 30 corresponding to the head-and-neck-contouring part 82 and the upper-femoral-shaft-contouring part 84 meet each other by a first angle and the outer portions 30 corresponding to the upper-femoral-shaft-contouring part 84 and the upper-femoral-shaft-holding part 86 meet each other by a second angle, such that the patient-specific instrument 100 holds the portion of head 96, neck 94, and upper shaft body 92 of the femur 90 substantially stably. In the illustrated embodiment, the first angle is larger than the second angle. It is much larger considering the holding portion 85.

The patient-specific instrument 100 may further comprise a head-holding part extending from the head-and-neck-contouring part 82 and following substantially up to a summit portion of the head 96, where the pelvis 99 meets with the head 96.

The upper-femoral-shaft-holding part 86 may be configured to go around a corner of the upper shaft 92 to the portion of the upper shaft 92 covered by the head-neck-area receiving inner portion 10 corresponding to the upper-femoral-shaft-contouring part 84.

The patient-specific instrument 100 is applicable to a plurality of surgical approaches incluisic anterior-posterior or lateral surgical hip approaches.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A patient-specific instrument for durable resurfacing hip replacement device, the patient-specific instrument comprising:

a head-neck-area receiving inner portion contoured to fit over a portion of head, neck, and upper shaft body of the femur, so as to maintain a stable spatial relationship with the femur;

a top edge portion extending from the head-neck-area receiving portion and configured for being substantially perpendicularly to a plane defined by the head, neck, and shaft body of the femur;

an outer portion extending from the top edge portion substantially perpendicularly to the top edge portion;

one or more femoral-shaft-hole guiding pins installed on the top edge portion, so as to work as a first reference line showing a first direction of a long nail portion of the durable resurfacing hip replacement device;

one or more distal-head-neck-hole guiding pins installed on the outer portion, so as to work as a second reference line showing a second direction of a lag screw portion of the durable resurfacing hip replacement device; and a vertical groove provided on the outer portion and aligned in parallel to at least one of the one or more femoral-shaft-hole guiding pins, wherein the one or more distal-head-neck-hole guiding pins, the one or more femoral-shaft-hole guiding pins, and the vertical groove are configured for helping a surgeon to install the durable resurfacing hip replacement device.

2. The patient-specific instrument of claim 1, wherein the patient-specific instrument is customized to an individual patient.

3. The patient-specific instrument of claim 2, wherein the head-neck-area receiving inner portion, the top edge portion, the one or more distal-head-neck-hole guiding pins, the femoral-shaft-hole guiding pin, and the vertical groove of the patient-specific instrument are customized by a computer navigated method.

4. The patient-specific instrument of claim 2, wherein the head-neck-area receiving inner portion of the patient-specific instrument is customized to the individual patient.

5. The patient-specific instrument of claim 2, wherein a contour of the head-neck-area receiving inner portion of the patient-specific instrument is determined and manufactured through an MRI/CT scan.

6. The patient-specific instrument of claim 1, wherein patient-specific instrument is made of plastic material.

7. The patient-specific instrument of claim 1, wherein the patient-specific instrument comprises:

a head-and-neck-contouring part;

an upper-femoral-shaft-contouring part extending from the head-and-neck-contouring part; and an upper-femoral-shaft-holding part extending from the upper-femoral-shaft-contouring part, wherein the outer portions corresponding to the head-and-neck-contouring part and the upper-femoral-shaft-contouring part meet each other by a first angle and the outer portions corresponding to the upper-femoral-shaft-contouring part and the upper-femoral-shaft-holding part meet each other by a second angle, such that the patient-specific instrument holds the portion of head, neck, and upper shaft body of the femur substantially stably.

8. The patient-specific instrument of claim 7, wherein the patient-specific instrument further comprises a head-holding part extending from the head-and-neck-contouring part and following substantially up to a summit portion of the head.

9. The patient-specific instrument of claim 7, wherein the upper-femoral-shaft-holding part is configured to go around a corner of the upper shaft to the portion of the upper shaft covered by the head-neck-area receiving inner portion corresponding to the upper-femural-shaft-contouring part.

10. The patient-specific instrument of claim 1, wherein the patient-specific instrument is applicable to a plurality of surgical approaches incluisic anterior-posterior or lateral surgical hip approaches.

* * * * *